United States Patent [19]

Kunstmann et al.

[11] 4,014,884
[45] Mar. 29, 1977

[54] BASICALLY SUBSTITUTED 3,4-DIHYDRO-2H-ISOQUINOLIN-1-THIONES

[75] Inventors: Rudolf Kunstmann, Breckenheim; Joachim Kaiser, Bad Soden, Taunus, both of Germany

[73] Assignee: Hoechst Aktiengesellschaft, Frankfurt am Main, Germany

[22] Filed: Aug. 12, 1975

[21] Appl. No.: 603,931

[30] Foreign Application Priority Data

Aug. 14, 1974 Germany .................. 2438965

[52] U.S. Cl. ............. 260/288 CE; 260/247.1 M; 260/283 S; 260/283 SY; 260/287 D; 260/288 D; 424/258
[51] Int. Cl.² ..................................... C07D 217/22
[58] Field of Search ..... 260/283 S, 288 D, 288 CE; 424/258

[56] References Cited

UNITED STATES PATENTS

| 3,644,366 | 2/1972 | Jeanmart et al. | 260/283 S |
| 3,753,994 | 8/1973 | Diana | 260/288 D |

FOREIGN PATENTS OR APPLICATIONS

| 1,126,155 | 9/1968 | United Kingdom | 260/283 S |

*Primary Examiner*—Donald G. Daus
*Assistant Examiner*—M. C. Vaughn
*Attorney, Agent, or Firm*—Curtis, Morris & Safford

[57] ABSTRACT

The invention relates to 3,4-dihydro-2H-isoquinolin-1-thiones and a process for preparing them.

The compounds have an antiarrhythmic activity and are suitable for treating disturbance of the cardiac rhythm.

5 Claims, No Drawings

BASICALLY SUBSTITUTED 3,4-DIHYDRO-2H-ISOQUINOLIN-1-THIONES 3,4-Dihydro-2H-isoquinolin-1-thiones having a neutral substituent are already known. In U.S. Pat. No. 3,644,366 and German Offenlegungsschriften Nos. 1,911,519 and 2,112,026 such compounds are described as intermediate products for the preparation of compositions acting on coronary circulation.

German Offenlegungsschrift No. 2,143,745 claims analogous compounds having a hypolipidemic activity.

Now 3,4-dihydro-2H-isoquinolin-1-thiones basically substituted in 4-position acting on coronary circulation have been found. Therefore, the invention relates to 3,4-dihydroisoquinolines of the formula I

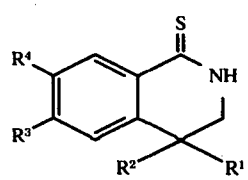

wherein $R_1$ is hydrogen, a saturated or unsaturated, straightchained or branched alkyl radical having 1 to 6 carbon atoms or the phenyl radical, $R_2$ is a dialkylaminoalkyl radical of the formula

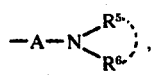

wherein A is a straight-chained or branched low molecular alkylene group and $R^5$ and $R^6$ are identical or different and are straight-chained or branched, low molecular alkyl radicals and may form together with the nitrogen atom a 5-, 6- or 7-membered ring, wherein one of the hydrocarbons is substituted by a hetero atom preferably the oxygen, sulfur or nitrogen atom optionally substituted by hydrogen, $C_1$ - $C_4$ - alkyl or the phenyl radical, $R^3$ and $R^4$ are identical or different and represent hydrogen or a lower alkoxy group having 1 to 4 carbon atoms, as well as the physiologically tolerable salts thereof.

Preferred substituents are for $R^1$ the methyl, ethyl or phenyl radical, for $R^2$ a dialkylaminoalkyl radical of the formula

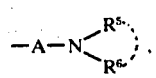

wherein A is a straight-chained or branched alkylene group having 2 ot 3 carbon atoms and $R^5$ and $R^6$ represent identical alkyl radicals having 1 to 4 carbon atoms or $R^5$ and $R^6$ represent together with the nitrogen atom a 5- or 6-membered ring or the morpholine radical, and for $R^3$ and $R^4$ hydrogen or the methoxy group.

The invention further relates to processes for preparing the compounds of the formula I as well as pharmaceutical compositions of these compounds.

The process for preparing the compounds of the invention comprises a. cycling a compound of the formula II a or II b

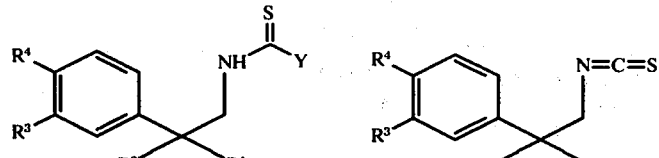

wherein $R^1$ to $R^4$ have the above meaning and Y is an optionally substituted amino group, O-alkyl or S-alkyl or S-phenyl radical, or b. replacing the oxygen atom, by an sulfur atom an in a usual manner in a compound of the formula III

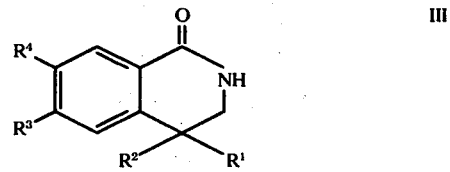

wherein $R^1$ to $R^4$ have the meaning mentioned in formula I

C. cycling an amino thioacid derivative of the formula IV

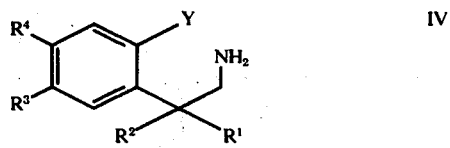

wherein $R^1$ to $R^4$ have the meaning mentioned in formula I and Y is a thiocarboxyl group or the derivative thereof, or a hydroxycarboxylic acid thioamide of the formula V

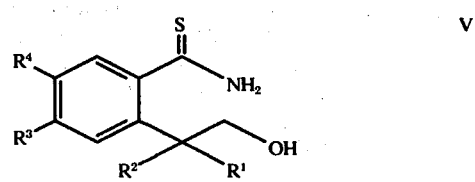

wherein $R^1$ to $R^4$ have the meaning mentioned in formula I, or d. cycling a N-hydroxyalkyl-substituted benzoic acid thioamide of the formula VI

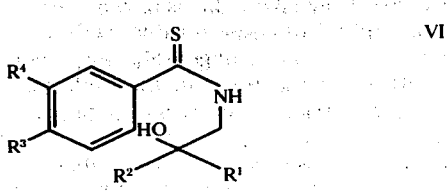

wherein R¹ to R⁴ have the meaning given in formula I, or e. introducing subsequently the substituents R¹ and/or R² by alkylation into a compound of the formula I, wherein R¹ and/or R² represent hydrogen and R³ and R⁴ have the meaning mentioned, or f. reacting with a secondary amine in a compound of the formula VII

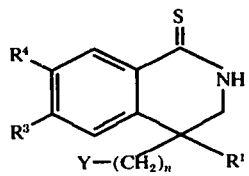

wherein R¹, R³ and R⁴ have the meaning given in formula I, and wherein n is an integer of from 1 to 4 and Y is a substituent which may be replaced by a secondary amine, or g. substituting subsequently the amino group in a compound of the formula VIII

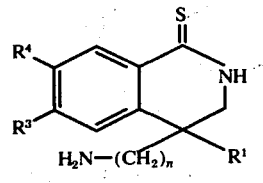

wherein R¹, R³ and R⁴ have the meaning given in formula I, and in which n is an integer of from 1 to 4, or h. cycling a compound of the formula IX

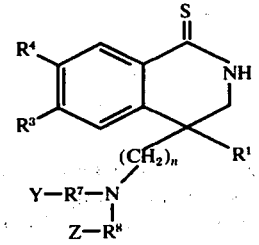

wherein R¹, R³ and R⁴ have the meaning given in formula I, n is an integer of from 1 to 4, R⁷ and R⁸ are a low molecular alkyl radical and Y and Z are the hydroxyl, mercapto or amino group, or j. cycling a compound of the formula IX, wherein R¹, R³, R⁴, r⁷, R⁸ and n have the mentioned meaning and Y and Z represent a radical which may be replaced by a primary amine or water, with a primary amine or by treatment with water.

The preparation of the starting materials of the formulae IIa and IIb for the method a) is effected via an amine of the formula X

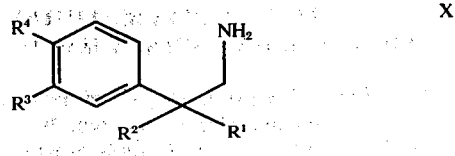

which may be prepared by catalytical hydrogenation of the corresponding nitrile of the formula XI

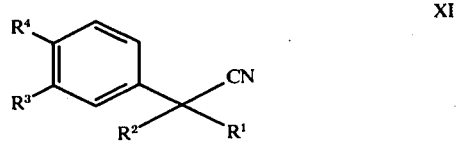

This nitrile may be obtained by alkylation of the corresponding benzyl cyanide of the formula XII

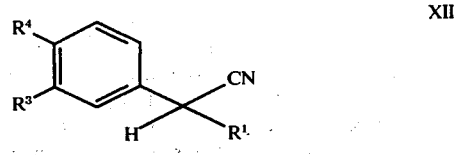

with an alkyl halide in the presence of sodium amide in an inert solvent, expediently according to the method described in Liebigs Annalen volume 561 (1949), page 52 (method A). The compounds of the formula XII may also be obtained according to this method from the corresponding benzyl cyanides (R¹ = H).

The preparation of diphenyl-acetonitriles (R¹ = phenyl), which carry substituents in one of the phenyl rings, is carried out according to a process of T. Kametani et al. (J. Org. Chem. 36, 327 (1971)). An ortho-halogenalkoxy-benzene is reacted with NaNH₂ in an inert solvent such as benzene, toluene or THF to obtain the corresponding dehydrobenzene, which adds benzyl cyanide in situ and yields the desired substituted derivative (method B).

The nitrile thus prepared of the formula XI is hydrogenated to an amine of the formula X in ethanol or methanol saturated with ammonia with Raney-Nickel as a catalyst, at a pressure of 70–120 atmospheres gauge and 100°–125° C during 8 to 36 hours. The operation is expediently carried out according to Org.Synth. 23, 71 (1943). The amine obtained of the formula X is converted according to usual methods into a derivative of the isothiocyanic acid IIa or IIb capable to ring closure.

The isothiocyanates IIb are prepared for example according to J. Am. Chem. Soc. 81, (1959) page 4328. The amines (X) are converted with CS₂ and a base (for example triethyl amine) in the presence of chloroformic acid esters into dithiocarbamic acid esters, which provide the corresponding isothiocyanates with a base in excess (for example triethyl amine). Or the amine (X) or the hydrochloride thereof is reacted with thiophosgene in the presence of a base such as Na₂CO₃ or CaCO₃ in an aqueous medium (cf. Houben-Weyl "Methoden der organischen Chemie", volume IX, 875 (1955)).

Thiocarbamic acid esters (IIa, Y = OR) are expediently prepared from the isothiocyanates (IIb) which are reacted with an alcohol or an alcoholate to the desired compounds at temperatures between 20° and 80° C without solvent or with an alcoholate dissolved in the corresponding alcohol. These methods are described for example in J. Am. Chem. Soc. 77, 581 (1955) or 65, 900, (1943).

The dithiocarbamic acid esters (II a, Y = S—R) may also be prepared from the isothiocyanates (IIb) by reaction with mercaptanes. The mercaptane is dissolved in a 20–30 % sodium hydroxide solution and the isothiocyanate is added dropwise and then acidified (cf. Chem. Abstr. (1910), 910).

To prepare the thio-ureas (IIa, Y = NH$_2$) the starting compound is for example the amine (X) which is reacted to the thiourea with ammonium rhodanide in the presence of a mineral acid (for example HCl) at elevated temperature (cf. Arzneimittel Forschg. 2, 125 (1952))—the operation may also be carried out in an inert solvent, for example chlorobenzene, which is saturated with HCl—or the isothiocyanate (IIb) is reacted to the thio-urea at room temperature in an aqueous alcoholic ammonia solution (cf. Chem. Ber. 80, 275 (1947)).

To prepare the differently substituted thioureas (IIa, Y=NH—R) the prescriptions of J. Am. Chem. Soc. 51, 1909 (1929), are followed, whereby the amine (X) is reacted under reflux with an isothiocyanate (IIb) with an amine without solvent or dissolved in alcohol. For thio-ureas (IIa, Y = NRR') the mustard oil (IIb) is reacted with a secondary amine at 0° C or under reflux in an inert solvent such as benzene, toluene, chlorobenzene or ethyl acetate (cf. Chem. Ber. 28, 2935 (1895)).

Among the preferred compounds of the formula II a there may be mentioned thiocarbymic acid esters (Y = O-alkyl having 1–4 carbon atoms or Y = O-phenyl) as well as thio-urea derivatives (Y = N-alkyl having 1 to 4carbon atoms or Y = N-phenyl).

Method a

The reaction according to method (a) is effected according to known methods. The compounds of the formula IIa or IIb are reacted in the presence of a catalyst with or without solvent. As catalysts there are preferably used anhydrous or practically anhydrous acid catalysts, preferably polyphosphoric acid, phosphoroxy chloride, concentrated sulfuric acid or Lewis acids, as for example AlCl$_3$. As solvents - as far as they are used for the reaction—there are considered inert anhydrous organic solvents, especially chlorinated hydrocarbons, as for example CCl$_4$ or trichloroethylene, furthermore CS$_2$ or aromatic hydrocarbons such as benzene, toluene or xylene. The temperatures applied depend on the reactants used and vary between −15°and 150° C.

Method b

The starting compounds of the formula III for the method b) are also prepared according to known methods. As starting materials are used compounds of the formulae IIa and IIb, which contain an oxygen atom instead of the sulfur atom. The preparation of these compounds is effected in analogous manner from the amines of the formula X.

Isocyanates are prepared for example from the amines (X) with phosgene in an inert solvent such as benzene, toluene, ethyl acetate or chlorobenzene, preferably as indicated in Org. Synth. Coll. Vol. II, 453 (1943) or Liebigs Ann. Chem. 562, 105, 106 (1049).

Carbamic acid esters (Y = OR) are prepared in the simplest way according to a modified method, described in Org. Synth. Coll. Vol. II, 278 (1943). In the presence of a base (for example Na$_2$CO$_3$) or NaOH) the amine is reacted with a chloroformic acid ester in an inert solvent such as toluene, benzene, chlorobenzene, ehtyl acetate or a chlorinated hydrocarbon such as CCl$_4$ at elevated temperature. Or the starting compounds are the isocyanates (IIb) and they are heated with the calculated amount of alcohol with or without addition of an inert solvent (benzene, ethyl acetate for example) (cf. J. Am. Chem. Soc. 62, 218 (1940).

To prepare the ureas for example the prescription of J. Am. Chem. Soc. 51, 1797 (1929) is followed. The amine of the formula X is reacted to urea with nitrourea in water or a water/alcohol mixture at room temperature or while heating gently. Alkylated ureas (Y = NHR or NRR') are prepared from the isocyanates with a primary or secundary amine in an inert solvent such as benzene, toluene, chlorobenzene or an aliphatic, chlorinated hydrocarbon according to R. 51, 432 (1932).

In order to convert the compounds of the formula III into the corresponding sulfur derivatives of the formula I according to method (b) known reactions are used. Especially suitable is the reaction with P$_4$S$_{10}$ in pyridine or toluene with or without addition of an acid-binding agent, as for example CaO or a compound of the formula III is reacted with PCl$_5$ in pyridine, benzene or toluene to obtain the imide chloride, which provides compounds of the formula I with H$_2$S or a thiourea, if desired after hydrolisis of the intermediately formed isothiuronium salt.

Method c

Aminothioacid derivatives of the formula IV and hydroxycarboxylic acid thioamides of the formula V which may be prepared according to one of the usual ways may be cycled with or without acidic catalysts as for example sulfuric acid or phosphoric acid, or with or without solvents splitting off water, as for example acetic acid anhydride or thionyl chloride, with or without solvents as for example glacial acetic acid, alcohol or ether at temperatures from room temperature to the boiling point of the solvent.

Method d

The reaction according to process (d) proceeds under the conditions indicated for process (a).

Method e

The subsequent introduction of the substituents R$^1$ and/or R$^2$ into the isoquinoline structure of the formula XIII according to process e)

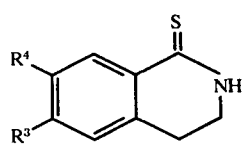

XIII is effected according to known methods; it is expedient to react with a suitable reagent as for example chloroformic acid ester under alkylating conditions, for example with alcoholate in alcohol or sodium amide in inert solvents such as benzene, or without base directly with the alkylating agent, whereby first the thioamide function is protected. Into the compound thus obtained of the formula XIV

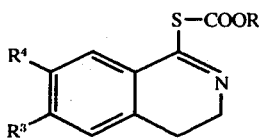

the substituents R¹ and/or R² are introduced by stepwise alkylation, preferably with sodium amide in inert solvents, for example benzene or toluene; it is not important if substitution is carried out first with R¹ or R². When using chloroformic acid ester as protective group the subsequent saponification and decarboxylation, preferably by treatment with acids or bases in water, alcohols or aqueous alcohols, lead to a compound of the formula I.

The compunds VII, VIII, IX which serve as starting compounds for the processes f, g, h and j according to the invention, may be synthetized according to known methods. They may also be prepared according to one of the ways of synthesis indicated under (a) to (e).

Method f

The reaction according to the process (f), whereby Y in VII preferably means a halogen atom such as Cl or J, or another radical capable of being substituted by a secondary amine, as for example the p-toluene sulfonic acid or methane sulfonic acid radical, is effected in the presence of an excess of the secondary amine to be used, or if the secondary amine is added in a stoichiometrical amount, with addition of a base, as for example sodium hydroxide solution, aqueous sodium carbonate solution, triethyl amine or alcoholat in suitable solvents, for example water, alcohols, for example methanol or butanol, ethers such as diethyl ether or dimethoxy ethylene, aromatic or aliphatic, optionally halogenated hydrocarbons, for example cyclohexane, chloroform, toluene or chlorobenzene, polar solvents such as dimethyl-sulfoxide or dimethylformamide or mixtures of the solvents mentioned at a temperature between room temperature and the boiling point of the solvent used.

Method g

The alkylation of a compound of the formula VIII according to process (g) works according to known methods, whereby preferably the alkylation with an alkyl ester of an organic or inorganic acid is used, for example dimethyl- or diethyl sulfate or a benzene-sulfonic acid alkyl ester (i.e. Org. Synth. 44, 72 (1964), Pharm. Chem. J. 193, (1969), or a compound of the formula VIII is subjected to a reaction with a corresponding alkyl compound, whereby the conditions indicated for the process (f) are applied. The two alkyl radicals may also be introduced successively. There is considered the reaction of the amine with an aldehyde or ketone to obtain the Schiff base, subsequent alkylation of the Schiff base and hydrogenation of the imonium salt. The prescription indicated in Chem. Inform. 16–258 (1973) is advantageously observed.

Method h

The compounds of the formula IX are cycled according to known methods. Cyclisation may be carried out in the presence of a catalyst, but also without catalyst, either in an inert solvent or without solvent. It is expedient that a compound of the formula IX is maintained in an inert solvent in the presence of an acid catalyst, preferably borotrifluoride etherate or p-toluene-sulfonic acid until the reaction is complete at temperatures between 0° C and the boiling point of the solvent used. As solvents there are considered preferably ethers such as tetrahydrofurane, dimethoxy-ethane or, if desired, chlorinated aliphatic or aromatic hydrocarbons such as cyclohexane, methylene chloride, chlorobenzene or toluene. If Y and/or Z represent the hydroxy group the reaction formed may preferably be separated with the aid of a water separator.

Method j

The reactions according to process (j) are preferably carried out at conditions indicated for the process (f). Y and Z represent in this case a radical which may be substituted by a secondary amine or water and represent for example chlorine or iodine or the p-toluene sulfonic acid or methane sulfonic acid radical.

Besides the compounds mentioned in the Examples the following compounds of the invention may be preferably used:

4-(2-Diethylaminoethyl)-3,4-dihydro-2H-isoquinolin-1-thione
4-(2-Dimethylaminopropyl)-3,4-dihydro-2H-isoquinolin-1-thione
4-(2-Diisopropylaminoethyl)-3,4-dihydro-2H-isoquinolin-1-thione
4-(2-Dimethylaminoethyl)-3,4-dihydro-2H-isoquinolin-1-thione
4-(2-Dibutylaminoethyl)-3,4-dihydro-2H-isoquinolin-1-thione
4-[2(1-Pyrrolidinyl)-ethyl]-3,4-dihydro-2H-isoquinolin-1-thione
4-[2(1-Piperidinyl)-ethyl]-3,4-dihydro-2H-isoquinolin-1-thione
4-Methyl-4-(2-dimethylaminoethyl)-3,4-dihydro-2H-isoquinolin-1-thione
4-Methyl-4-(2-diethylaminoethyl)-3,4-dihydro-2H-isoquinoline-1-thione
4-Methyl-4-(2-diisopropylaminoethyl)-3,4-dihydro-2H-isoquinolin-1-thione
4-Methyl-4-[2-(1-pyrrolidinyl)-ethyl]-3,4-dihydro-2H-isoquinolin-1-thione
4-Ethyl-(2-dimethylaminoethyl)-3,4-dihydro-2H-isoquinolin-1-thione
4-Ethyl-4-(2-diisopropylaminoethyl)-3,4-dihydro-2H-isoquinolin-1-thione
4-Ethyl-4-[2-(1-pyrrolidinyl)ethyl]-3,4-dihydro-2H-isoquinolin-1-thione
4-Propyl-4-(2-dimethylaminoethyl)-3,4-dihydro-2H-isoquinolin-1-thione
4-Propyl-4-(2-diethylaminoethyl)-3,4-dihydro-2H-isoquinolin-1-thione
4-Propyl-4-(2-diisopropylaminoethyl)-3,4-dihydro-2H-isoquinolin-1-thione
4-Propyl-4-[2-(1-pyrrolidinyl)-ethyl]-3,4-dihydro-2H-isoquinolin-1-thione
4-Propyl-4-[2-(1-piperidinyl)-ethyl]-3,4-dihydro-2H-isoquinolin-1-thione
6-Methoxy-4-(2-diethylaminoethyl)-3,4-dihydro-2H-isoquinolin-1-thione
6-Methoxy-4-(2-dimethylaminopropyl)-3,4-dihydro-2H-isoquinolin-1-thione
6-Methoxy-4-(2-diisopropylaminoethyl)-3,4-dihydro-2H-isoquinolin-1-thione
6-Methoxy-4-(2-dimethylaminoethyl)-3,4-dihydro-2H-isoquinolin-1-thione 6-Methoxy-4-(2-dibutylaminoethyl)-3,4-dihydro-2H-isoquinolin-1-thione
6-methoxy-4-[2-(1-pyrrolidinyl)-ethyl]-3,4-dihydro-2H-isoquinolin-1-thione
6-Methoxy-4-[2-(1-piperidinyl)-ethyl]-3,4-dihydro-2H-isoquinolin-1-thione
6-Methoxy-4-methyl-4-(2-dimethylaminoethyl)-3,4-dihydro-2H-isoquinolin-1-thione
6-Methoxy-4-methyl-4-(2-diethylaminoethyl)-3,4-dihydro-2H-isoquinolin-1-thione
6-Methoxy-4-methyl-4-(2-diisopropylaminoethyl)-3,4-dihydro-2H-isoquinoline-1-thione
6-Methoxy-4-methyl-4-[2-(1-pyrrolidinyl)-ethyl]-3,4-dihydro-2H-isoquinolin-1-thione
6-Methoxy-4-methyl-4-[2-(1-piperidinyl)-ethyl]-3,4-dihydro-2H-isoquinolin-1-thione
6-Methoxy-4-ethyl-4-(2-dimethylaminoethyl)-3,4-dihydro-2H-isoquinolin-1-thione
6-Methoxy-4-ethyl-4-(2-diethylaminoethyl)-3,4-dihydro-2H-isoquinolin-1-thione
6-Methoxy-4-ethyl-4-(2-diisopropylaminoethyl)-3,4-dihydro-2H-isoquinolin-1-thione
6-Methoxy-4-ethyl-4-[2-(1-pyrrolidinyl)-ethyl]-3,4-dihydro-2H-isoquinolin-1-thione
6-methoxy-4-ethyl-4-[2-(1-piperidinyl)-ethyl]-3,4-dihydro-2H-isoquinolin-1thione
6-Methoxy-4-propyl-4-(2-dimethylaminoethyl)-3,4-dihydro-2H-isoquinolin-1-thione
6-Methoxy-4-propyl-4-(2-diethylaminoethyl)-3,4-dihydro-2H-isoquinolin-1-thione
6-Methoxy-4-propyl-4-(2-diisopropylaminoethyl)-3,4-dihydro-2H-isochinolin-1-thione
6-Methoxy-4-propyl-4-[2-(1-pyrrolidinyl)-ethyl]-3,4-dihydro-2H-isoquinolin-1-thione
6-Methoxy-4-propyl-4-[2-(1-piperidinyl)-ethyl]-3,4-dihydro-2H-isoquinolin-1-thione
6,7-Dimethoxy-4-(2-dimethylaminopropyl)-3,4-dihydro-2H-isoquinoline-1thione
6,7-Dimethoxy-4-(2-diisopropylaminoethyl)-3,4-dihydro-2H-isoquinolin-1-thione
6,7-Dimethoxy-4-(2-dimethylaminoethyl)-3,4-dihydro-2H-isoquinolin-1-thione
6,7-Dimethoxy-4-(2-dibutylaminoethyl)-3,4-dihydro-2H-isoquinolin-1-thione
6,7-Dimethoxy-4-[2-(1-pyrrolidinyl)-ethyl]-3,4-dihydro-2H-isoquinolin-1-thione
6,7-Dimethoxy-4-[2-(1-piperidinyl)-ethyl]-3,4-dihydro-2H-isoquinolin-1-thione
6,7-Dimethoxy-4-methyl-4-(2-dimethylaminoethyl)-3,4-dihydro-2H-isoquinolin-1-thione
6,7-Dimethoxy-4-methyl-4-(2-diethylaminoethyl)-3,4-dihydro-2H-isoquinolin-1thione
6,7-Dimethoxy-4-methyl-4-(2-diisopropylaminoethyl)-3,4-dihydro-2H-isoquinolin-1-thione
6,7-Dimethoxy-4-methyl-4-[2-(1-pyrrolidinyl)-ethyl]-3,4-dihydro-2H-isoquinolin-1-thione
6,7-Dimethoxy-4-methyl-4-[2-(1-piperidinyl)-ethyl]-3,4-dihydro-2H-isoquinolin-1thione
6.7-Dimethoxy-4-ethyl-4-(2-dimethylaminoethyl)-3,4-dihydro-2H-isoquinolin-1-thione
6,7 Dimethoxy-4-ethyl-4-(2-diethylaminoethyl)-3,4-dihydro-2H-isoquinolin-1-thione
6,7-Dimethoxy-4-ethyl-4-(2-diisopropylaminoethyl)-3,4-dihydro-2H-isoquinolin-1-thione
6,7-Dimethoxy-4-ethyl-4-[2-(1-pyrrolidinyl)-ethyl]-3,4-dihydro-2H-isoquinolin-1-thione
6,7-Dimethoxy-4-ethyl-4-[2-(1-piperidinyl)-ethyl]-3,4-dihydro-2H-isoquinolin-1-thione
6,7-Dimethoxy-4-propyl-4-(2-dimethylaminoethyl)-3,4-dihydro-2H-isoquinolin-1-thione
6,7-Dimethoxy-4-propyl-4-(2-Diethylaminoethyl)-3,4-dihydro-2H-isoquinolin-1-thione
6,7-Dimethoxy-4-propyl-4-(2-diisopropylaminoethyl)-3,4-dihydro-2H-isoquinolin-1-thione
6,7-Dimethoxy-4-propyl-4-[2-(1-pyrrolidinyl)-ethyl]-3,4-dihydro-2H-isoquinolin-1-thione
6,7-Dimethoxy-4-propyl-4-[2-(1-piperidinyl)-ethyl]-3,4-dihydro-2H-isoquinolin-1-thione
6-Methoxy-4-phenyl-4-(2-dimethylaminoethyl)-3,4-dihydro-2H-isoquinolin-1-thione
6-Methoxy-4-phenyl-4-(2-diethylaminoethyl)-3,4-dihydro-2H-isoquinolin-1-thione
6-Methoxy-4-phenyl-4-[2-(1-pyrrolidinyl)-ethyl]-3,4-dihydro-2H-isoquinolin-1-thione
6-Methoxy-4-phenyl-4-[2-(1-piperidinyl)-ethyl]-3,4-dihydro-2H-isoquinolin-1-thione
6-Methoxy-4-phenyl-4-[2-(1-morpholinyl)-ethyl]-3,4-dihydro-2H-isoquinolin-1-thione
6,7-Dimethoxy-4-phenyl-4-(2-dimethylaminoethyl)-3,4-dihydro-2H-isoquinolin-1-thione
6,7-Dimethoxy-4-phenyl-4-82-diethylaminoethyl)-3,4-dihydro-2H-isoquinolin-1-thione
6,7-Dimethoxy-4-phenyl-4-(2-diisopropylaminoethyl)-3,4-dihydro-2H-isoquinolin-1-thione
6,7-Dimethoxy-4-phenyl-4-[2-(1-pyrrolidinyl)-ethyl]-3,4-dihydro-2H-isoquinolin-1-thione
6,7-Dimethoxy-4-phenyl-4-[2-(1-piperidinyl)-ethyl]-3,4-dihydro-2H-isoquinolin-1-thione
6,7-Dimethoxy-4-phenyl-4-[2-(1-morpholinyl)-ethyl]-3,4-dihydro-2H-isoquinolin-1-thione The compounds of the invention have valuable therapeutical properties. Thus, besides other pharmacological properties they have an action on coronary circulation which shows itself particularly in an antiarrhythmic activity. These compounds are, thus, suitable for the treatment of disturbances of the cardiac rhythm. The antiarrhythmic activity was detected on isolated papillary muscles of guinea pigs and dogs to which strophantin has been administered.

The novel compounds of the invention may be used either individually or mixed with pharmacologically compatible carriers. For oral administration the active compounds are mixed with the suitable substances and brought by usual methods into suitable administration forms such as tablets, gelatin capsules, aqueous, alcoholic or oily suspensions or aqueous alcoholic or oily solutions. A inert carriers there may be used for example magnesium carbonate, lactose or mais starch with addition of other substances, as for example magnesium stearate. The preparation may be carried out as dry or moist granules. As oily carriers or solvents there are especially considered vegetable and animal oils, as for example sunflower oil or cod-liver oil.

A special administration form is the intravenous administration. For this purpose the active compounds or the physiologically tolerable salts thereof are brought to dissolution with the usual substances. Such physiologically tolerable salts are formed for example with the following acids; hydrochloric acid, hydrobromic acid or hydriodic acid, phosphoric acid, sulfuric acid, methylsulfuric acid, amidosulfonic acid, nitric acid, formic acid, acetic acid, propionic acid, succinic acid, tartric acid, lactic acid, malonic acid, fumaric acid, oxalic acid, citric acid, malic acid, mucic acid, benzoic acid, salicylic acid, aceturic acid, embonic acid, naphthalene-1,5-disulfonic acid, ascorbic acid, phenylacetic acid, p-amino-salicylic acid, hydroxyethane-sulfonic acid, benzene-sulfonic acid or synthetic resins containing acid groups, for example those having the effect of ion exchangers.

As solvents of the corresponding physiologically tolerable salts of the active compounds for intravenous administration there may be mentioned for example: water, physiological sodium chloride solution or alcohols such as for example ethanol, propane-diol or glycerol, furthermore sugar solutions as for example glucose or mannitol solutions or a mixture of the different solvents mentioned.

The dosage unit for a human being is for intravenous administration mg to 50 mg/kg, preferred 1 mg to 10 mg/kg, for oral administration 2 to 300 mg/kg, preferred 10 mg to 50 mg/kg.

As daily dosage there may be considered for i.v. administration 0.3 mg to 500 mg/kg, preferably 1 mg to 50 mg/kg, for oral administration 2 mg to 500 mg/kg, preferably 10 mg to 150 mg/kg.

The following Examples illustrate the invention.

EXAMPLE 1

4-(3-Dimethylaminopropyl)-4-phenyl-3,4-dihydro-2H-isoquinolin-1-one a. 2,2-Diphenyl-5-dimethylaminopentyl-isothiocyanate To a stirred solution of (0.35 mol) of 2,2-diphenyl-5-dimethyl-aminopentylaminohydrochloride in 140 ml of dry chloroform 10 ml (0.77 mol) of triethyl amine were added dropwise. At −10° C a solution of 25.0 ml (0.41 mol) of carbon disulfide in 100 ml of chloroform were added while stirring within 30 minutes and stirring was continued for 1 hour. Then, at 0° C, a solution of 40.0 ml (0.41 mol) of chloroformic acid ethyl ester in 70.0 ml of chloroform were added within 30 minutes and stirring was continued at room temperature for 1 hour. Then a solution of 57.0 ml (0.41 mol) of triethyl amine in 140 ml of chloroform were added during 15 minutes and stirring was continued for 1 hour. After addition of 420 ml of chloroform a clear solution was obtained which was washed twice with a 5% sodium hydroxide solution and a 5% hydrochloric acid and water in each case. After drying with $Na_2SO_4$ the whole was evaporated and the crude isothiocyanate was immediately further reacted.

b. 4-(3-Dimethylaminopropyl)-4-phenyl-3,4-dihydro-2H-isoquinolin-1-thione 0.30 Mol of crude 2,2-diphenyl-5-dimethylamino-pentyl-isothiocyanate was introduced within 30 minutes into 500 ml of concentrated sulfuric acid with stirring and cooling, whereby the reaction temperature should not exceed 40° C. Stirring was continued at room temperature for one hour. The reaction solution was subsequently poured as a thin jet onto 5.0 l of ice water and the alkaline aqueous phase was extracted with chloroform. The solution was dried with $Na_2SO_4$, evaporated and the residue was tritutated with ethanol.

Melting point: 212° C (oxalate).

c. 4-(3-Dimethylaminopropyl)-4-phenyl-3,4-dihydro-2H-isoquinolin-1-thione 10 mmols of 2,2-diphenyl-5-dimethylamino-pentylisothiocyanate were added dropwise to a suspension of 15 mmols of aluminium chloride in 3.0 ml of carbon disulfine at room temperature and refluxed for 15 minutes. Then 10 ml of water were added dropwise while cooling and adjusted to an alkaline medium. The product was extracted with benzene, dried and the solvent was evaporated in vacuo. The amorphous residue was tritutated with ethyl acetate and the crystals suction-filtered.

Melting point: 210°–213° C (oxalate).

d. 4-(3-Dimethylaminopropyl)-4-phenyl-3,4-dihydro-2H-isoquinolin-1-thione 3.7 mmols of 2,2-diphenyl-5-dimethylaminopentyl-isothiocyanate and 7.5 mmols of aluminum chloride were triturated well and allowed to stand for 24 hours at room temperature. Then water was added carefully with cooling, the whole was extracted with benzene, dried and concentrated.

Melting point: 211° C (oxalate).

EXAMPLE 2

4-(3-Dimethylamino-2-methyl-propyl)-4-phenyl-3,4-dihydro-2H-isoquinolin-1-thione From 2,2-diphenyl-4-methyl-5-dimethylamino-pentyl-amine in analogy to 1a and subsequent to 1b.

Melting point: 215° C (oxalate).

EXAMPLE 3

4-(3-Piperidin-1-yl-propyl)-4-phenyl-3,4dihydro-2H-iso-1-thione a. N-(2,2-diphenyl-5-piperidin-1-yl-n-pentyl)-carbamic acid ethyl ester 0.25 mol of 2,2-diphenyl-5-piperidino-1-yl-n-pentyl-amino-hydrochloride was suspended in 650 ml of toluene and 71.6 g 0.68 mol) of anhydrous sodium carbonate. 46.4 g (0.43 mol) of chloroformic acid ethyl ester were added dropwise, while stirring, and the whole was refluxed for 5 hours. It was suction-filtered from the undissolved material and the filtrate was concentrated in vacuo. The urethane was further reacted in a crude state.

b. 4-(3-Piperidin-1-yl-propyl)-4-phenyl-3,4-dihydro-2H-isoquinolin-1-one 0.2 Mol of N-(2,2-diphenyl-5-piperidin-1-yl-n-pentyl)-carbamic acid ethyl ester was introduced into 500 ml of hot (130° C) and stirred polyphosphoric acid so that the temperature was kept between 130° and 140° C. The temperature was kept for 10 minutes at 140° C and after cooling the mixture was poured onto 70°–80° C in 2.0 l of ice water. After standing over night the water was decanted and the residue was extracted twice with water. The water phase was adjusted to an alkaline range, extracted with benzene, dried and concentrated in vacuo. The remaining oil was dissolved in about 40 ml of methanol and brought to crystallization by addition of seed crystals.

Melting point: 184°–185° C (oxalate).

c. 2,2-Diphenyl-5-piperidino-1-yl-n-pentyl-isocyanate 0.1 Mol of 2,2-diphenyl-5-piperidin-1-yl-n-pentyl-aminohydro-chloride were introduced into 200 ml of 1 m solution of phosgene in toluene and refluxed for 10 hours. After cooling the mixture was extracted with water, adjusted to an alkaline range, extracted with $CHCl_3$, dried and evaporated. The isocyanate was further reacted in a crude state.

d. 4-(3-Piperidin-1-yl-propyl)-4-phenyl-3,4-dihydro-2H-isquinolin-1-one 20 mmols of crude 2,2-diphenyl-5-piperidino-1-yl-n-pentyl-isocyanate were added dropwise, while stirring, to a suspension of 2.9 g (22 mmols) of aluminum chloride in 20 ml of 1,2-dichloro-ethane and the temperature was kept below 30° C.

Stirring was continued for one hour at room temperature and the mixture was carefully mixed with 30 ml of water and adjusted to an alkaline range. After addition of 20 ml of dichloroethane the organic phase was separated, dried and concentrated. The residue was dissolved in 20 ml of methanol, filtered from the undissolved material and the solvent was evaporated. Crystals from a small amount of methanol were obtained.
Melting point: 183°–184° C (oxalate).

e. 4-(3-Piperidino-1yl-propyl)-4-phenyl-3,4-dihydro-2H-isoquinolin-1-one 1.08 mols of N-(2,2-diphenyl-5-piperidino-1-yl-n-penytl)-carbamic acid ethyl ester were refluxed for 3 hours in 2.2 l of phosphoroxy chloride. The phosphoroxy chloride in excess was distilled in vacuo and the residue was poured onto ice water. The alkaline range was adjusted with concentrated sodium hydroxide solution. The product was extracted with benzene, washed with water, dried and concentrated.
Melting point: 182°–184° C (oxalate).

f. 4-(3-Piperidin-1-yl-propyl-4-phenyl-3,4-dihydro-2H-isoquinolin-1-thione 90 mmols of 4,(3-piperidino-1-yl-propyl-4 -phenyl-3,4-dihydro-2H-isoquinolin-1-one (cf. Example 3 e) were dissolved in 35 ml of pyridine and 9.0 g (40 mmols) of phosphorpentasulfide were added while stirring. The solution was refluxed for 4 hours and after cooling poured into 400 ml of water. The pH value was adjusted to 8–8.5 with a 10 % potassium hydroxide solution and stirring was continued for 4 hours. After suction-filtering the mixture was washed with water. The product was dried at the air and recrystallized from ethanol/dimethylformamide (4:1).
Melting point: 130°–135° C (oxalate).

g. 4-(3-piperidino-1-yl-propyl)-4-phenyl-3,4-dihydro-2H-isoquinolin-1-thione 20 mmols of 4-(3-piperidino-1-yl-propyl)-4-phenyl-3,4-dihydro-2H-isoquinolin-1-one (cf. Example 3e) were introduced into a suspension of 1.8 g (8 mmols) of phosphorpentasulfide and 1.8 g (32 mmols) of calcium oxide in 50 ml of toluene, while stirring, and refluxed for 6 hours. The hot toluene solution was decanted from the resin residue through a filter and the resin was extracted twice with 50 ml of benzene in each case. The combined organic solutions were concentrated in vacuo and the remaining oil was triturated with ethanol and then recrystallized from ethanol/dimethylformamide (4:1).
Melting point: 131°–133° C (oxalate).

h. 4-(3-Piperidino-1-yl-propyl)-4-phenyl-3,4-dihydro-2H-isoquinolin-1-thione 20 mmols of 4-(3-piperidino-1-yl-propyl-4-phenyl-3,4-dihydro-2H-isoquinolin-1-one (cf. Example 3e) were introduced into a suspension of 4.2 g (20 mmols) of phosphorpentachloride in 20 ml of toluene and then refluxed for 3 hours. Then H₂S was introduced at room temperature until the development of HCl had finished. The solvent was eliminated in vacuo and the residue was triturated with ethanol.

Melting point: 131°–135° C (oxalate).

EXAMPLE 4

4-(2-Piperidino-1-yl-ethyl)-4-phenyl-3,4-dihydro-2H-isoquinolin-1-thione

From 2,2-diphenyl-4-piperidino-1-yl-butyl amine in analogy to 1a and subsequently 1b.
Melting point: 148°–150° C (oxalate).

EXAMPLE 5

4-(2-Diisopropylaminoethyl)-4-phenyl-3,4-dihydro-2H-isoquinolin-1-thione

From 2,2-diphenyl-4-diisopropylamino-butyl-amine in analogy to 1a and subsequently 1b.
Melting point: 139°–141° C.

EXAMPLE 6

4-(2-Di-n-butylaminoethyl)-4-phenyl-3,4-dihydro-2H-isoquinolin-1-thione

From 2,2-diphenyl-4-di-n-butylaminobutyl-amine in analogy to 1a and subsequently 1b.
Melting point: 110° C (oxalate).

EXAMPLE 7

4-(2-dietylaminoethyl)-4-phenyl-3,4-dihydro-2H-isoquinolin-1-thione

From 2,2-diphenyl-4-diethylaminobutyl amine in analogy to 1a and subsequently 1b.
Melting point: 170° (oxalate).

EXAMPLE 8

4-(2-Piperidino-1-yl-ethyl)-4-ethyl-3,4-dihydro-2H-isoquinolin-1-thione

From 2-ethyl-2-phenyl-4-piperidino-1-yl-butyl amine in analogy to 1a and subsequently 1b.
Melting point: 302°–305° (HCl).

EXAMPLE 9

4-(2-diethylaminoethyl)-4-ethyl-3,4-dihydro-2H-isoquinolin-1-thione

From 2-ethyl-2-phenyl-4-diethylamino-butyl amine in analogy to 1a and subsequently 1b
Melting point: 132°–135° C (oxalate).

EXAMPLE 10

4-(2-Diisopropylaminoethyl)-4-phenyl-6-methoxy-3,4-dihydro-2H-isoquinolin-1-thione From 2-phenyl-2-(3-methoxyphenyl)-4-diethylaminobutylamine in analogy to 1a and subsequently 1b.
Melting point: 177° C (HCl).

EXAMPLE 11

4-(2-diethylaminoethyl)-6,7-dimethoxy-3,4-dihydro-2H-isoquinolin-1-thione

From 2-(3,4-dimethoxyphenyl)-4-diethylamino-butyl amine in analogy to 1a and subsequently 1b.
Melting point: 138°–141° C (oxalate).

EXAMPLE 12

4-(3-dimethylamino-2-methyl-propyl)-3,4-dihydro-2H-isoquinolin-1-thione

From 2-phenyl-4-methyl-5-dimethylamino-pentyl amine in analogy to 1a and subsequently 1b.

EXAMPLE 13

4-(2-Piperidino-ethyl)-4-methyl-3,4-dihydro-2H-isoquinolin-1-thione

From 2-phenyl-2-methyl-4-piperidino-1-yl-butyl amine in analogy to 1a and subsequently 1b.

Melting point: 227°–230° C (HCl).

EXAMPLE 14

4-(3-Dimethylaminopropyl)-4-methyl-3,4-dihydro-2H-isoquinolin-1-thione

From 2-phenyl-2-methyl-5-dimethylamino-pentylamine in analogy to 1a and subsequently 1b.

Melting point: 113°–115° C.

The starting compounds of the formulae X and XI for the preparation of the compounds of formula I described in the preceding Examples 1 to 14 are listed in the following Tables 1 and 2, respectively.

TABLE 1

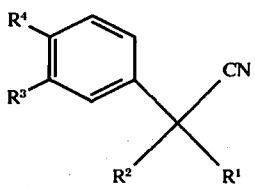
XI

| | $R^1$ | $R^2$ | $R^3$ | $R^4$ | Method | bp/mp in ° C |
|---|---|---|---|---|---|---|
| 1) | $C_6H_5$ | $-(CH_2)_3-N(CH_3)_2$ | H | H | A | mp: 66° C |
| 2) | $C_6H_5$ | $-CH_2-CH(CH_3)-CH_2-N(CH_3)_2$ | H | H | A | mp: 55° C |
| 3) | $C_6H_5$ | $-(CH_2)_3-N\langle piperidino \rangle$ | H | H | A | crude product |
| 4) | $C_6H_5$ | $-(CH_2)_2-N\langle piperidino \rangle$ | H | H | A | mp: 74–76° C |
| 5) | $C_6H_5$ | $-(CH_2)_2-N(i-C_3H_7)_2$ | H | H | A | bp: 175–182° C/ 0,3 mmHg |
| 6) | $C_6H_5$ | $-(CH_2)_2-N(n-C_4H_9)_2$ | H | H | A | bp: 185–186° C/ 0,7 mmHg |
| 7) | $C_6H_5$ | $-(CH_2)_2-N(C_2H_5)_2$ | H | H | A | bp: 155–165° C/ 0,5 mmHg |
| 8) | $C_2H_5$ | $-(CH_2)_2-N\langle piperidino \rangle$ | H | H | A | bp: 143–145° C/ 1,0 mmHg |
| 9) | $C_2H_5$ | $-(CH_2)_2-N(C_2H_5)_2$ | H | H | A | bp: 126–128° C/ 0,7 mmHg |
| 10) | $C_6H_5$ | $-(CH_2)_2-N(i-C_3H_7)_2$ | $OCH_3$ | H | B | bp: 180–185° C/ 0,5 mmHg |
| 11) | H | $-(CH_2)_2-N(C_2H_5)_2$ | $OCH_3$ | $OCH_3$ | A | bp: 175–179° C/ 0,6 mmHg |
| 12) | H | $-CH_2-CH(CH_3)-CH_2-N(CH_3)_2$ | H | H | A | bp: 131–135° C/ 1,0 mmHg |
| 13) | $CH_3$ | $-(CH_2)_2-N\langle piperidino \rangle$ | H | H | A | bp: 162–165° C/ 2 mmHg |
| 14) | $CH_3$ | $-(CH_2)_3-N(CH_3)_2$ | H | H | A | bp: 130–135° C/ 1,5 mmHg |

TABLE 2

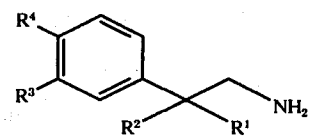

| | $R^1$ | $R^2$ | $R^3$ | $R^4$ | mp (in ° C)/ | (NMR) in ppm |
|---|---|---|---|---|---|---|
| 1) | $C_6H_5$ | $-(CH_2)_3-N(CH_3)_2$ | H | H | | crude product |
| | | | | | $CH_3$:s | 2,05 (6 prot.) |
| | | | | | $NH_2$:s | 1,4 (2 prot.) |
| 2) | $C_6H_5$ | $-CH-CH(CH_3)-CH_2-N(CH_3)_2$ | H | H | | crude product |
| | | | | | $CH_3$:s | 2,1 (6 prot.) |
| | | | | | $CH_3$:d | 1,6 (3 prot.) |

TABLE 2-continued

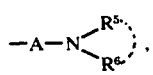

| R¹ | R² | R³ | R⁴ | mp (in °C)/ | (NMR) in ppm |
|---|---|---|---|---|---|
| 3) C₆H₅ | —(CH₂)₃—N⟨piperidine⟩ | H | H | | crude product C₆H₅:m 7,2–7,6 (10 prot.) aliphat.:m 0,95–3,15 (18 prot.) |
| 4) C₆H₅ | —(CH₂)₂—N⟨piperidine⟩ | H | H | F: 93–94° C | |
| 5) C₆H₅ | —(CH₂)₂—N(i—C₃H₇)₂ | H | H | mp: 58° C | |
| 6) C₆H₅ | —(CH₂)₂—N(n—C₄H₉)₂ | H | H | | crude product CH₃:t 1,12 (6 prot.) |
| 7) C₆H₅ | —(CH₂)₂—N(C₂H₅)₂ | H | H | | crude product CH₃:t 1,1 (6 prot.) |
| 8) CH₃ | —(CH₂)₂—N(C₂H₅)₂ | H | H | | crude product CH₃:t 1,05 (6 prot.) CH₃:s 1,4 (3 prot.) |
| 9) C₂H₅ | —(CH₂)₂—N(C₂H₅)₂ | H | H | | crude product CH₃:m 0,8–1,4 (9 prot.) |
| 10) C₆H₅ | —(CH₂)₂—N(i—C₃H₇)₂ | OCH₃ | H | | crude product CH₃:d 1,3 (12 prot.) OCH₃:s 3,8 (3 prot.) |
| 11) H | —(CH₂)₂—N(C₂H₅)₂ | OCH₃ | OCH₃ | | CH: m crude product 4,05 (1 prot.) OCH₃:s 3,9 (6 prot.) |
| 12) H | —CH₂—CH(CH₃)—CH₂—N(CH₃)₂ | H | H | | crude product CH₃:s 2,1 (6 prot.) CH₃:d 1,4 (3 prot.) |
| 13) CH₃ | —(CH₂)₂—N⟨piperidine⟩ | H | H | | crude product CH₃:s 1,1 (3 prot.) |
| 14) CH₃ | —(CH₂)₃—N(CH₃)₂ | H | H | | crude product CH₃:s 2,05 (6 prot.) |

What we claim is:

1. A 3,4-dihydroisoquinoline of the formula I

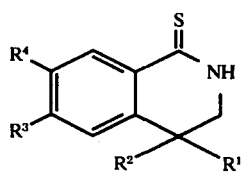

wherein R¹ is hydrogen, saturated straight-chained or branched alkyl having 1 to 6 carbon atoms or phenyl, R₂ is dialkylaminoalkyl of the formula $$-A-N\begin{matrix}R^5 \\ R^6\end{matrix},$$

wherein A is straight-chained or branched low molecular alkylene having 2–3 carbon atoms and R⁵ and R⁶ are identical or different and are straight-chained or branched, low molecular alkyl having 1–4 carbon atoms and may form together with the nitrogen atom a 5- or 6-membered ring, R³ and R⁴ are identical or different and are hydrogen or lower alkoxy having 1 to 4 carbon atoms as well as the physiologically tolerable salts thereof.

2. The compound as claimed in claim 1, which is 4-(2-piperidino-1-yl-ethyl)-4-phenyl-3,4-dihydro-2H-isoquinolin-1-thione.

3. The compound as claimed in claim 1, which is 4-(2-diethylaminoethyl)-6,7-dimethoxy-3,4-dihydro-2H-isoquinoline-1-thione.

4. A pharmaceutical composition having antiarrhythmic activity which comprises an effective amount of a compound as claimed in claim 1 together with a pharmacologically compatible carrier.

5. A pharmaceutical composition as defined in claim 4 wherein the carrier is an inert carrier selected from the group consisting of magnesium carbonate, lactose and mais starch.

* * * * *